United States Patent [19]
Siegel

[11] Patent Number: 5,062,269
[45] Date of Patent: Nov. 5, 1991

[54] DISPOSABLE BODY COOLER

[76] Inventor: Israel Siegel, 2980 Point East Dr., N. Miami Beach, Fla. 33160

[21] Appl. No.: 656,458

[22] Filed: Feb. 19, 1991

[51] Int. Cl.[5] .................... F25D 5/02

[52] U.S. Cl. .................... 62/4; 62/259.3; 126/204; 126/263

[58] Field of Search .................... 62/4, 259.3; 126/204, 126/263

[56] References Cited

U.S. PATENT DOCUMENTS

| | | | |
|---|---|---|---|
| 2,429,973 | 11/1947 | Alexander | 126/204 |
| 2,855,758 | 10/1958 | Johnson | 62/4 |
| 3,296,819 | 1/1967 | Gough | 62/259.3 |
| 3,320,682 | 5/1967 | Sliman | 126/263 |
| 3,950,158 | 4/1976 | Gossett | 62/4 |
| 4,118,946 | 10/1978 | Tubin | 126/204 |

*Primary Examiner*—Albert W. Davis, Jr.

[57] ABSTRACT

A solid emdothermic reactant is distributed in flexible tubes adapted to fit body contour. Means are provided to fix the solid endothermic reactant in evenly distributed spots in the coils. The tubes are adapted to be worn like a vest in close proximity to body surfaces. When a cooling effect is desired water is added to the tubes to initiate the endothermic cooling reactions.

8 Claims, 1 Drawing Sheet

DISPOSABLE BODY COOLER

BACKGROUND AND OBJECTIVES

The invention relates to cooling devices and in particular to a cooling system that is wearable. Existing air conditioning systems are designed to cool building spaces and can not be conveniently used to cool an individual who moves outdoors. The main objective of the present invention is to provide a direct body cooling system that can be used both indoors and outdoors and can travel with the person using the cooling system. Other objectives consist of a provision of a cooling system that is readily accessible, is of very light weight, and disposable because it and contains no complex or expensive components. Another objective of the invention is provide a direct cooling of a person using the cooling system and, thus, reduce the energy required for cooling of building spaces.

SUMMARY

The invention is based upon the principle that certain solid substances induce an endothermic reaction and absorb heat from the environment when dissolved in water. It consists of a disposable cooling system that can be worn like a vest, and travel with the person using the cooling system. The vest consists of a series of intercommunicating horizontal tubes. Present between the horizontal tubes are a series of vertical tubes. The vertical tubes open at their upper end into bottom portion of the horizontal tubes. The lower end of the vertical tubes is closed and is not connected to the horizontal tubes. Present inside the vertical tubes are granules of amonium nitrate. The granules are fixed in the vertical tubes by screens which prevent the exit of the granules from the vertical tubes, but allow the passage of liquids into the tubes. The vest is attached to the body by a series of adjustable straps. Present outside of the vest is a standard portable canteen containing water. The cooling action of the vest is initiated by the transfer of water from the canteen into the coils of the vest through a tube which communicates with the coils.

DETAILED DESCRIPTION

Figure 1:
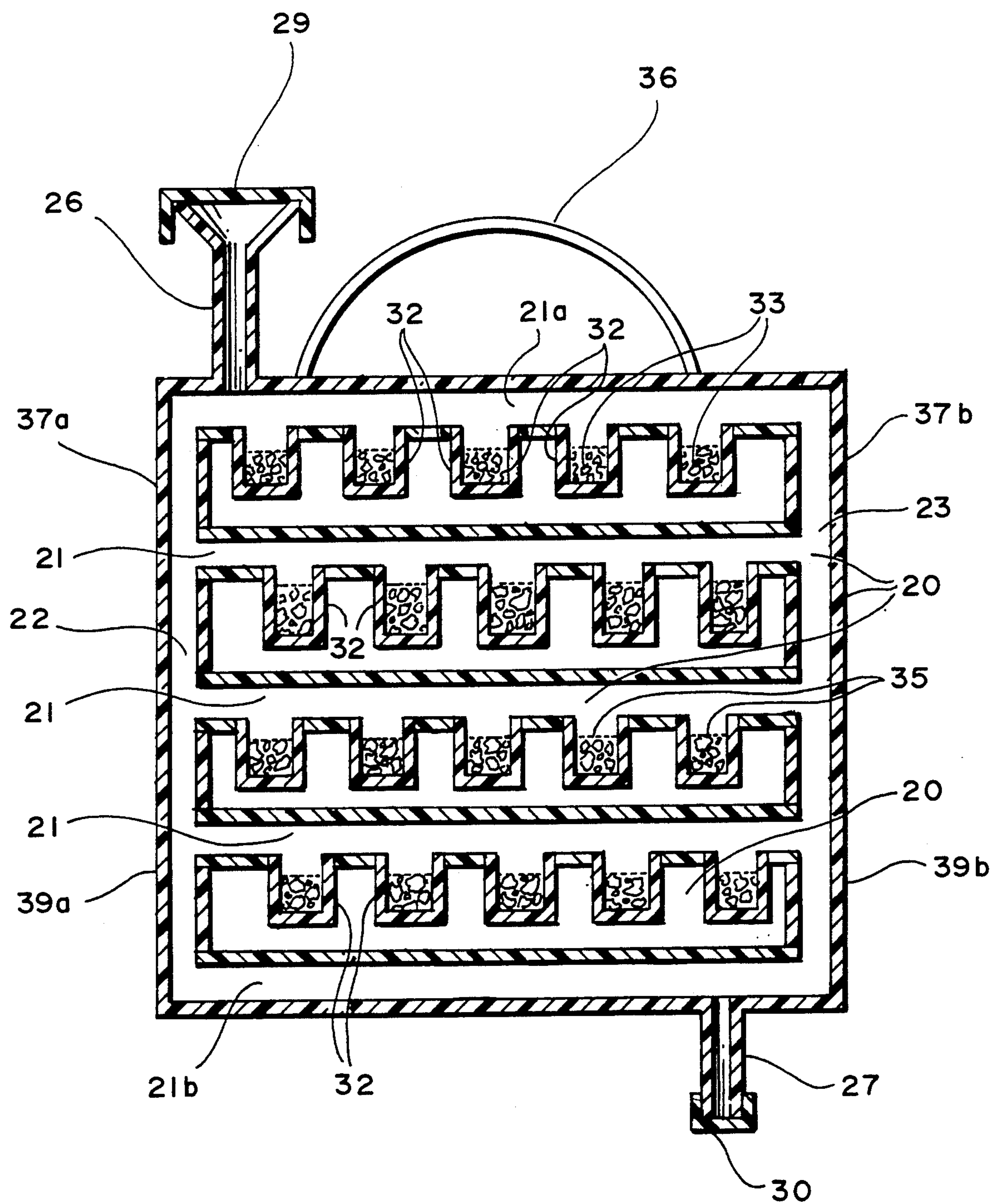
FIG. 1 is a cross sectional view of an embodiment of a wearable air conditioner.

FIG. 1 illustrates the basic structures of an embodiment of a cooling vest 20. As shown in the figure, there is present a series of inter-communicating containers. The containers consist of a series of horizontal tubes 21. The horizontal tubes include a top horizontal tube 21*a* and a bottom horizontal tube 21*b*. The arrangement is that all the horizontal tubes open into side vertical tubes 22 and 23. Communicating with the top horizontal tube 21*a* is an inlet tube 26. As seen the top of inlet tube 26 is shaped like a funnel to facilitate the intake of water into tube 26. Communicating with bottom horizontal tube 11*b* is an outlet tube 27. A removable cover 29 open and closes inlet tube 26. A removable cover 30 opens and closes outlet tube 27.

Present between horizontal tubes 21 are vertical tubes 32. The arrangement is that the vertical tubes open at their upper end into bottom portion of the horizontal tubes. The lower end of the vertical tubes is closed and is not connected to the horizontal tubes. The length of the vertical tubes is such that they fit between the spaces of the horizontal tubes. Present inside vertical tubes 32 are granules of amonium nitrate 33. The amonium nitrate granules function to induce an endothermic reaction upon the addition of water, as will be explained. Present on top of tubes 32 are screens 35. The arrangement is that the holes of the screens are smaller than the diameter of granules 33. The screens serve to prevent the exit of the granules from the vertical tubes, but to allow the passage of liquids into the tubes. The vertical tubes thus form pockets which serve to fix granules 33 in fixed even positions. The horizontal and vertical tubes 21 and 32 have a very large surface volume ratio, are flexible, and shaped to resemble a vest which fits body contour. For example, tubes 21 and 32 may consist of flexible nylon coils. A strap 36 is attached to the top horizontal tube 21*a*. The arrangement is that the strap forms a loop that can be worn on the neck of the person using the body cooler. Attached to the side top corner of tube 22 is a strap 37*a*. Attached to the side top corner of tube 23 is a strap 37*b*. The straps are adapted to loop around the back of the person in opposite directions, and to be tied to each other. The length of the straps 37*a* and 37*b* is such that they as they loop around the back of the person using the vest they pull the vest in opposing directions. They, thus, stretch the flexible horizontal tubings 21 and induce an even spread of the upper portion of vertical tubes 32 around the upper front body surfaces of the person wearing the vest. Attached to the bottom side corner of tube 22 is a strap 39*a*. Attached to the bottom side corner of tube 23 is a strap 39*b*. The straps are adapted to loop around the back of the person in opposing directions, and to be tied to each other. The length of straps 39*a* and 39*b* is such that they as they loop around the back of the person using the vest they pull the vest in opposing directions. They, thus, stretch the flexible horizontal tubings 21 and induce an even spread of the lower portion of vertical tubes 32 around the lower front body of the person wearing the vest. Present outside of the vest is a standard portable water canteen (not shown). The canteen contains water, and is carried by the person (not shown) using the vest.

The operation of the device by the person wearing the device is as follows. For a direct body heat removal the vest is worn in close proximity to body surfaces. For example, the vest may be worn on top of the undershirt of the person using the cooling device. The vest is positioned horizontally on the front surface of the person using the vest through strap 36 which fits around the neck of the person using the vest. The vest is then positioned vertically by straps 37*a*, 37*b*, 39*a*, and 39*b*. When a cooling effect is desired cover 29 is removed and water, obtained from a portable canteen, or other sources, is poured into tube 26. The amount or water used would depend on the sizes of tubes 11 and 20, on the type of the solid endothermic component used, and on the amount and duration of cooling required. For example, a total of about 24 thousand calories would be removed from the environment by a cooling mixture containing 500 ml of water and 500 g of ammonium chloride (Handbook of Chemistry and Physics, 44th edition, 1962, page 2403). The number and dimensions of tubes 11 and 20 should be planned to accomodate the volume of the cooling mixtures.

While the present embodiment described a vest which fits around the front of the body it is understood that a similar vest may be adapted to fit around the back of the body. The front and back vests may be worn simultaneously to obtain a cooling system which completely surrounds most of the body's surfaces. Other details such as the shape and composition of coils 21 and pockets 32 or the chemical composition of the endothermic components, may be altered without departing from the essence of the invention as set forth in the claims.

What is claimed is:

1. A disposable wearable cooling device said device consist of a network of inter-communicating containers,
said containers adapted to fit body contour,
a solid component which induces an endothermic reaction when mixed with water distributed in said containers,
means to fix said solid component in pre-determined locations in said containers to obtain an even distribution of said solid component in said containers,
and a reversible communication of said containers with the outside environment to allow the addition of water to said solid endothermic component.

2. The invention as described in claim 1 and including a portable source of water.

3. The invention as described in claim 1 wherein said means to localize said solid in said coils consist of pockets to hold said solid component.

4. The invention as described in claim 3 and including barriers which prevent the passage of a solid from said pockets but allows passage of liquids to said pockets.

5. The invention as described in claim 1 and including means to place said body cooler in close proximity to body surfaces.

6. The invention as described in claim 1 wherein said containers are flexible and inlude means to stretch said flexible containers.

7. An endothermic cooling mixture consisting of at least one solid and one liquid component,
said solid component distributed in a network of inter-communicating containers,
means to localize said solid component in pre-determined locations in said containers,
means to place said liquid reactant outside of said containers,
and a reversible communication of said containers with the outside environment to allow a mixing of said solid and said liquid reactants.

8. The invention as described in claim 7 wherein said containers are adapted to fit body contour.

* * * * *